United States Patent [19]

Stapp

[11] 4,237,312

[45] Dec. 2, 1980

[54] OXIDATION PROCESS INCLUDING RECOVERY AND RECYCLE OF CATALYST

[75] Inventor: Paul R. Stapp, Bartlesville, Okla.

[73] Assignee: Phillips Petroleum Company, Bartlesville, Okla.

[21] Appl. No.: 26,388

[22] Filed: Apr. 2, 1979

[51] Int. Cl.$^3$ ............................................. C07C 67/05
[52] U.S. Cl. .................. 560/246; 260/410.6; 260/464; 260/465 D; 260/465.4; 560/1; 560/83; 560/84; 560/85; 560/89; 560/102; 560/106; 560/107; 560/111; 560/112; 560/193; 560/194; 560/183; 560/197; 560/198; 560/228; 560/230
[58] Field of Search ..................... 560/244, 246, 1, 83, 560/84, 85, 89, 102, 106, 107, 111, 112, 193, 194, 183, 197, 198, 228, 230; 260/410.6, 464, 465 D, 465.4

[56] References Cited

U.S. PATENT DOCUMENTS

| | | | |
|---|---|---|---|
| 3,420,873 | 1/1969 | Olivier | 560/243 |
| 3,542,857 | 11/1970 | Lutz | |
| 3,595,905 | 7/1971 | Schultz | |
| 3,723,510 | 3/1973 | Ono | 560/246 |
| 3,742,039 | 6/1973 | Ono | |
| 3,755,423 | 8/1973 | Onoda | |
| 3,872,164 | 3/1975 | Schmidt | 560/246 |
| 3,907,874 | 9/1975 | Harvey | 560/246 |
| 3,920,736 | 11/1975 | Gaenzler | |
| 3,922,300 | 11/1975 | Onoda | 560/244 |
| 4,013,583 | 3/1977 | Knifton | |
| 4,044,041 | 8/1977 | Stapp | 560/244 |
| 4,100,362 | 7/1978 | Stapp | 560/244 |
| 4,122,285 | 10/1978 | Weitz | 560/244 |

FOREIGN PATENT DOCUMENTS

| | | | |
|---|---|---|---|
| 50-71614 | 6/1975 | Japan | |
| 51-108013 | 9/1976 | Japan | 560/244 |
| 1138366 | 1/1969 | United Kingdom | |
| 1170222 | 11/1969 | United Kingdom | |

OTHER PUBLICATIONS

Inagaki, Chem. Abst. 75:129289d (1971).

*Primary Examiner*—Natalie Trousof
*Assistant Examiner*—Michael Shippen

[57] ABSTRACT

In the oxidation of acyclic conjugated dienes, recovery and recycle of the oxidation catalyst is accomplished by distilling off the oxidation solvent, extraction of the oxidation product with a suitable solvent, and removal of the extraction solvent residue from the catalyst, and recycle of the catalyst to the oxidation step.

19 Claims, No Drawings

OXIDATION PROCESS INCLUDING RECOVERY AND RECYCLE OF CATALYST

FIELD OF THE INVENTION

The invention pertains to the conversion of acyclic conjugated dienes to diesters. In another aspect, the invention pertains to the recovery and recycle of oxidation catalysts employed in the conversion process.

BACKGROUND OF THE INVENTION

Conjugated dienes, such as butadiene, present intriguing possible sources of a variety of more valuable chemicals, intermediates, and end-products. Such unsaturated compounds, obtained from various sources such as the conversion of or extraction from refinery streams produced in the modern integrated refinery and chemical processing operation sometimes terms a petrocomplex are still relatively cheap chemicals and upgrading thereof has economic advantages.

A number of oxidation processes have been developed using a variety of catalyst systems for the conversion of conjugated dienes, particularly acyclic conjugated dienes, to diesters (diacyloxyolefin).

Further needed, to provide economic viability for such processes, are methods for the recovery of the oxidation catalyst in a form or condition suitable for recycle and thus reuse in the oxidation step.

BRIEF DESCRIPTION OF THE INVENTION

I have discovered a process for the oxidation of an acyclic conjugated diene with steps for the recovery and recycle of the oxidation catalyst.

The oxidation step employs a catalyst system comprising (A) a copper or antimony component compound, (B) at least one alkali metal component compound, and (C) at least one halide component compound, effective to oxidize in carboxylic acid media the conjugated diene to form a diester. In recovering of the oxidation catalyst, remaining carboxylic acid media is distilled from the reaction mixture; the residual reaction admixture is extracted with a solvent to remove oxidation products, and this step requires a critical efficiency in the separation; the extract is distilled to separate this solvent for further use in the extracting step and to recover the oxidation product; and the catalyst is recycled to the oxidation step.

DETAILED DESCRIPTION OF THE INVENTION

In the process of my invention, at least one acyclic diolefin is oxidized in carboxylic acid media employing a catalyst system comprising (A) at least one copper or antimony compound, (B) at least one alkali metal ion-supplying compound, and (C) a halide-supplying compound, with molecular oxygen, and effective process conditions of temperature, pressure, and time, to produce an oxidation reaction product admixture compressing unreacted components, catalyst residues, and diacyloxy olefin product. In accordance with my process, the reaction product mixture is treated to recover for recycle unreacted components and catalyst residues.

Conjugated Diolefins

The conjugated diolefins are acyclic, and can be substituted or unsubstituted. There does not presently appear to be any limitation on molecular size except convenience and availability. From the latter standpoint, these acyclic conjugated dienes normally contain 4 to 16 carbon atoms per molecule.

The acyclic conjugated diolefins correspond to the general formula:

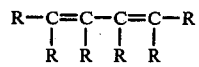

$$R-C=C-C=C-R \quad (I)$$
$$\phantom{R-}|\phantom{=C}|\phantom{-C}|\phantom{=C}|$$
$$\phantom{R-C=}R\phantom{-}R\phantom{-}R\phantom{=C-}R$$

In the above formula, each R is hydrogen, halogen, cyano, —COOR', or a monovalent hydrocarbyl radical which can be alkyl, aryl, cycloalkyl, or combination thereof such as aralkyl, or alkaryl. R' is hydrogen or an alkyl or aryl radical, of preferably not over 10 carbon atoms. The halogen can be any of fluorine, chlorine, bromine, or iodine. The total number of carbon atoms in all substituents preferably should not exceed about 12 because of considerations of availability, cost, and reactivity. For these reasons, the acyclic conjugated hydrocarbon dienes of 4 to 8 carbon atoms are preferred.

Examples of suitable acyclic conjugated dienes include 1,3-butadiene, 2-methyl-1,3-butadiene (isoprene), 2-chloro-1,3-butadiene, 2-ethyl-1,3-butadiene, 2-chloro-3-methyl-1,3-butadiene, 1,4-diphenyl-1,3-butadiene, 1,3-hexadiene, 1,3-pentadiene, 1,3-octadiene, 2-cyano-1,3-butadiene, 2-cyclohexyl-1,3-butadiene, 2-methylene-3-butenoic acid, and 2,4-pentadienenitrile. Presently preferred are 1,3-butadiene and isoprene because of availability, reactivity, and cost.

Catalyst System

The catalyst system employed in the oxidation/recovery/recycle process of my invention for the conversion of acyclic conjugated diolefins in carboxyic acid media to diacyloxyolefins comprises: (A) at least one component selected from the group consisting of (a) copper compounds, and (b) antimony compounds, (B) at least one alkali metal ion-supplying compound, and (C) at least one halide component. Presently preferably, a catalyst system will consist essentially of the aforesaid components.

The (A) component, can be either (a) a copper compound or (b) an antimony compound, or a mixture of two or more from either or both groups.

Where the (a) copper component is used, the copper ion can be either cuprous or cupric. Any copper compound can be used that provides a source of copper ion, including such as any of the chlorides, bromides, oxides, carbonates, carboxylates of such as up to 18 carbon atoms per molecule, nitrate, orthophosphates, sulfates, and the like. Examples of suitable copper compounds include copper(II) acetate, copper(I) bromide, copper(II) bromide, copper(II) benzoate, copper(II) butanoate, copper(I) chloride, copper(II) chloride, copper(II) dodecanoate, copper(II) octadecanoate, copper(I) oxide, copper(II) salicylate, copper(I) carbonate, copper(I) sulfate, copper(II) sulfate, copper(II) nitrate, copper(II) orthophosphate, and the like.

Wherein the (b) antimony component is to be employed, any antimony compound can be used including the chlorides, bromides, oxides, carboxylates of such as up to 18 carbon atoms per molecule, nitrates, sulfates, and the like. Examples of suitable antimony compounds include antimony tribromide, antimony trichloride, antimony pentachloride, antimony pentoxide, antimony trioxide, antimony(III) sulfate, and antimony trinitrate.

For the (B) component, any alkali metal compound which supplies the alkali metal ion can be used so long as it is suitable and effective, and is sufficiently soluble in the carboxylic acid media as to contribute the desired alkali metal ion. The alkali metal can be any one or more of lithium, sodium, potassium, rubidium, and cesium, though lithium presently is preferred since the lithium compounds are usually more soluble than their congeners in the reaction media.

Typical suitable alkali metal compounds include the halides, nitrates, carboxylates, oxides, hydroxides, carbonates, orthophosphates, sulfates, and the like, alone or in admixture. Examples of suitable alkali metal compounds include lithium chloride, lithium bromide, lithium nitrate, lithium acetate, lithium benzoate, lithium hydroxide, lithium oxide, lithium orthophosphate, lithium octadecanoate, lithium sulfate, sodium chloride, sodium bromide, sodium acetate, sodium nitrate, sodium sulfate, potassium chloride, potassium acetate, potassium nitrate, potassium benzoate, potassium sulfate, rubidium chloride, rubidium nitrate, rubidium bromide, rubidium acetate, rubidium sulfate, cesium chloride, cesium acetate, cesium nitrate, cesium sulfate, cesium oxide, and the like.

The (C) component of the catalyst system is a source of halide ion, specifically chloride or bromide, or mixture. The halide ion can be supplied, of course, by the (A) copper or antimony compound, or by the (B) alkali metal compound, or by other halide source compounds. Such other source halide compounds include the alkaline earth metal halides, or other halides whose cation is substantially inert under reaction conditions, or by organic halides such as the dihaloolefins wherein the halogen is in an allylic position with relation to the olefinic unsaturation in such haloolefins.

Exemplary halide ion sources include such as magnesium chloride, calcium bromide, strontium bromide, barium chloride, or such as 1,4-dibromo-2-butene, 1,4-dichloro-2-butene, and the like.

In the catalyst system employed, an appropriate exemplary molar ratio of (B):(A) alkali metal ion:copper or antimony is in the range of about 0.1:1 to 100:1, and presently preferably about 1:1 to 10:1 for best catalyst effectiveness, though the broad range should be considered exemplary and not limitative, since the oxidative step and process is operable outside of the broad range.

The molar ratio of (C):(A) halide ion:copper or antimony employed also presently for exemplary purposes should be in the range of about 0.1:1 to 100:1, presently preferably about 1:1 to 15:1 for best catalyst effectiveness, though again the broad range should be considered exemplary and not limitative since operability does lie outside of the broad range.

The catalyst concentration employed can be expressed conveniently in terms of the amount of (A) copper or antimony employed relative to the amount of acyclic conjugated diolefin charged to the reaction mixture. The ratios can range widely, so long as effective for oxidation results as desired. Presently considered exemplary is an amount of the (A) copper or antimony compound in the range of about 0.01 up to about 1 mole per mole of conjugated diene, presently preferable about 0.02 to 0.5 moles of copper or antimony per mole of conjugated diene because of considerations of cost and efficiency.

Carboxylic Acid Media

The term carboxylic acid media includes the use of mono or dicarboxylic acids alone, the anhydrides alone, or admixture of any of these. The carboxylic acid media employed in the process includes monocarboxylic acids, dicarboxylic acids, aliphatic as well as aromatic acids. These carboxylic acids form the ester moiety in the final olefinic product in the process of this invention.

The monocarboxylic acids can be represented by the general formula

and the dicarboxylic acids can be represented by the general formula:

In the formulae indicated above, $R''$ represents an alkyl, cycloalkyl, aryl, or combination radical such as alkaryl, aralkyl, or cycloalkylaryl, as well as a variety of substituted derivatives thereof including halogen, cyano, —COOR', in which the radicals can contain up to 4 substituents. $R'$ is as previously defined.

$R'''$ represents a valence bond, or alkylene, cycloalkylene, arylene, or combination radical such as alkarylene, cycloalkylarylene, or aralkylene. These radicals further can contain a variety of substituents as described for $R''$ above, since such substituents are essentially inert to the conditions and reactants employed in the process.

Exemplary carboxylic acids include such as acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, oxalic acid, succinic acid, adipic acid, terephthalic acid, tetrabromo-1,4-benzenedicarboxylic acid, tetracyano-1,4-benzenedicarboxylic acid, tetramethoxycarbonyl-1,4-benzenedicarboxylic acid, 2-decyloxycarbonylhexanedioic acid, 2-bromobutanoic acid, ethyl hydrogen adipate, 4-chlorobenzoic acid, 4-cyanobenzoic acid, 2-cyclohexylbenzoic acid, 2,3,4,5-tetrachlorobenzoic acid, ethyl hydrogen-o-phthalate, 4,6,8,10-tetracyanoundecanoic acid, 4,6,8,10-tetramethoxycarbonylundecanoic acid, 4-decyloxycarbonylcyclohexanecarboxylic acid, and the like, or their corresponding anhydrides. Acetic acid is a presently preferred carboxylic acid, because it is readily available, inexpensive, reactive, and easily handled. The carboxylic acid media employed preferably and conveniently is one characterized as normally liquid for convenience in handling under the conditions of the reaction.

It is convenient to employ the organic acid reactant media in large excess to serve as both reactant and reaction diluent for the oxidation step. Exemplarily, the amount of acid employed can be from an equimolar amount up to a molar ratio of about 500:1 relative to the conjugated diene. Preferably, the molar ratio of acid media to conjugated diene is about 2:1 to 10:1. One mole of anhydride is considered equivalent to two moles of acid.

Those acids or anhydrides which are normally solid, e.g. those which melt at temperatures above room temperature or thereabouts, can be employed either in a molten state or in essentially solid state at the initial stages of the reaction. As more product forms (which normally are liquid materials), such products function as solvents for any undissolved acid reactant and thereby promote dissolution of the acid in the reaction mixture. Conveniently, the conjugated diene also exerts a solubilizing effect on the solid acids/anhydrides and thus promotes a fluid mixture for the reaction system.

Water normally is a product of the oxidation reaction. Water present in the reaction mixture can hydrolyze the ester products of the reaction and thereby complicate product separation and reaction mixture workup. It thus is desirable to maintain an essentially anhydrous reaction system. One convenient way to assure this condition is to employ in admixture with the organic acid the corresponding anhydride of said acid. Any water present can react with the anhydride to form organic acid and thereby consume the water. The use of anhydride as a part of the carboxylic acid media thus is a preferred mode. The amount of anhydride employed can vary widely, though generally will be in the range of about 0.01 to 5 moles of anhydride per mole of organic acid employed.

Reaction Conditions

The oxidative step is carried out in the presence of molecular oxygen. The amount of oxygen present is not believed to be critical, though it is recognized that an undesirably slow reaction may result if the concentration of the molecular oxygen is very low. Pure oxygen can be employed, or mixtures of oxygen with inert gases such as air can be employed as a convenient source of oxygen.

It is recognized that explosive conditions can be obtained if the amount of molecular oxygen added into the reaction system is not adequately controlled. The process of the invention, as is true with many oxidation reactions, is highly exothermic and this aspect dictates caution in adding molecular oxygen to the reaction system. It is best to add the molecular oxygen incrementally or continuously during the reaction to avoid reaching an explosive range of oxygen concentration, as well as to allow better control of the temperature of the reaction. A reaction vessel equipped with efficient mixing means is desirable to avoid buildup to potentially dangerous concentrations of free oxygen. The reaction can be carried out under an oxygen pressure as convenient, such as about 0.1 to 1000, preferably about 5 to 200, psig of oxygen autogenous pressure obtained at the reaction temperature being maintained.

The oxidation step preferably is carried out in the liquid phase with all reactants and components substantially in the liquid phase, except of course the oxygen.

The oxidation step can be carried out at any convenient temperature so long as the temperature is effective for reaction, and not so high as to be unduly hazardous. Temperatures employed can range widely, so long as sufficient to maintain effective reaction rates. Exemplary temperatures are about +30° C. to 200° C., more preferably about 70° C. to 175° C., from considerations of balancing reaction rates and selectivity for desired products.

Time employed in the oxidative step is not critical, and can range widely, generally depending on the desired degree of conversion of the starting acyclic conjugated diolefin. An exemplary broad range is about 0.1 to 12 hours.

Catalyst Recovery and Recycle

The reaction mixture resulting from the catalytic oxidation of the acyclic conjugated diolefin comprises unreacted components, catalyst residues, and diacyloxy olefin product. The unreacted components primary are excess carboxylic acid media, unreacted diolefin, and residual oxygen. The reaction admixture is treated both to isolate the desired reaction product, as well as to recover the catalyst components for recycle to the oxidation step. This recovery and recycle is accomplished in a series of primary steps:

1. Distillation of the reaction mixture to remove unreacted carboxylic acid media, as well as to remove any unreacted oxygen and/or conjugated diene. Each of these components can be recycled.

2. The remaining reaction mixture is extracted with a solvent (extractant) suitable to remove oxidation products from the mixture as an extract. The solvent required is one that exhibits a high solubility toward the oxidation products, and in which the catalyst components are of a very low solubility. Separation of this extract then leaves the catalyst as a residue containing traces of extractant.

3. The extract is distilled to separate solvent for recycle for further extraction, and to recover the oxidation product.

4. The residual catalyst from the extraction step can be treated as necessary, such as by passing air over it to remove traces of extraction solvent, to avoid any accumulation of extraction solvent in the oxidation mixture. Further catalyst components, if necessary, can be added to maintain a suitable balance. The recovered catalyst is recycled to the oxidation step.

In the process of catalyst and product recovery, the reactor normally is vented if a batch reactor, or the reactor effluent is vented in a continuous process, to remove any unreacted molecular oxygen, and any unreacted conjugated diene, which can be separately recovered for recycle to the oxidation step, leaving a vented or stripped reaction admixture.

Thereafter, the reaction mixture is distilled to recover carboxylic acid media from the reaction mixture, leaving a remaining reaction admixture comprising products of oxidation and catalyst residues. The so-separated carboxylic acid media, acid, anhydride, or both, can be recycled, along with any additional carboxylic acid or anhydride as necessary to maintain desired ratios. Any convenient apparatus, such as a distillation column, can be used, at either atmospheric or reduced pressure as may be dictated by the particular carboxylic acid media employed. Any remaining unreacted acyclic conjugated diene recovered in this step also can be recycled to oxidation.

The reaction mixture residue from distillation is extracted with a solvent suitable and effective to solubilize and remove the products of oxidation as an extract, leaving catalyst from the residues. The nature of the extraction solvent is critical in my process to an efficient separation, requiring that the oxidation product have a high solubility in the solvent, and that the catalyst components have a low solubility in the solvent to avoid loss of the catalyst components.

Suitable solvents for the extraction step include unsubstituted or alkyl-substituted (one or more alkyl groups containing one to six carbon atoms per group) aromatics and alkylhalides. Examples of suitable aromatic solvents include benzene, toluene, o-xylene, m- xylene, -xylene, and the like, and mixtures thereof. The alkyl halide solvents can contain 1 to 12 carbon atoms and 1 to 8 bromine or chlorine or combination thereof atoms per molecule. Examples of suitable alkyl halide solvents include chloroform, carbon tetrachloride, methylene chloride, n-propyl chloride, n-butyl chloride, n-butyl bromide, 1-chlorohexane, 2-chlorohexane, 1,2-dichloroethane, 1,1,2,2-tetrachloroethane, 1,1,2,2-tetrachlorohexane, cyclohexyl bromide, cyclohexyl chloride, 1,2-dichlorocyclohexane (cis- or trans-), 1-chlorooctane, 1-bromooctane, 1-chlorododecane, and the like. Mixtures with the aromatics can be used. The solvent chosen should preferably have a boiling point sufficiently different from the boiling points of the products of oxidation to allow separation by distillation, and should be a liquid at room temperature for convenience in handling.

The quantity of solvent to be used will be that quantity needed to dissolve the oxidation product without dissolving a significant amount of the catalyst system. Although the amount of solvent used will depend on the nature of the solvent and the oxidation products, the amount will generally be about 0.5 to 50 volumes of solvent per volume of oxidation product, and for convenience in handling preferably about 2 to 10 volumes of solvent per volume of oxidation product.

The extract containing the products of oxidation and the solvent is separated from the insoluble catalyst residues by suitable incantations, decantation, filtration, or the like.

The catalyst residues obtained after separation of the extract then can be recycled as such. However, the separated catalyst residues usually contain traces of extraction solvent. Preferably, the separated catalyst residues are dried, such as passing air or other gas such as dry nitrogen over the residues to assist in removing traces of the extraction solvent, prior to recycle. This avoids accumulation of extraction solvent in the oxidation mixture. Where desired, the catalyst residue can be mildly heated such as about 30° to 60° C. to assist in the solvent stripping operation.

Various of the catalyst components can be added either to the catalyst residue, or directly to the oxidation zone, in order to maintain desired catalyst ratios.

The extract from the solubilizing step is treated for separation of the oxidation product, such as by fractional distillation to recover solvent for recycle to the solvent extraction step, and to recover the product or products of the oxidation process itself. Although the distillation can be at reduced pressure, the solvent usually can be removed satisfactorily at atmospheric pressures. The crude oxidation products separately distill at reduced pressure for recovery of pure fractions as may be desired for various commercial purposes.

EXAMPLES

The examples following are intended to assist one skilled in the art to a further understanding of my invention. Particular species, amounts, ratios, and other relationships, are intended to be exemplary of my invention but not limitative of the scope thereof.

EXAMPLE I

A series of runs was carried out utilizing 1,3-butadiene as the acyclic conjugated diene reactant with cupric acetate monohydrate, lithium bromide, and 1,4-dibromo-2-butene as the catalyst system and benzene as the extraction solvent to demonstrate the catalyst recovery and recycle process of my invention. In each of these runs, a 250 ml Fischer-Porter aerosol compatibility bottle equipped with a magnetic stirrer was used as the reactor.

In Run 1, cupric acetate monohydrate (9.6 g., 48 mmoles), lithium bromide (6.5 g., 75 mmoles), 1,4-dibromo-2-butene (2.3 g., 10.7 mmoles) and amounts of acetic acid and acetic anhydride shown in Table I were charged to the reactor, followed by the addition of 1,3-butadiene to the reactor in the vapor phase in amount as shown in Table I. The reactor was placed in an oil bath, pressured to 30 psig with oxygen, and heated to 140° C. over a period of about 1 hour. The reaction was continued at 140° C. for about 5–6 hours during which time at about 10 to 30 minute intervals the reactor was repressured to 120 psig with oxygen.

At the conclusion of the reaction period, the reactor was vented and the reaction mixture processed. The reaction mixture was transferred to a distilling flask and was distilled through an 18″ (46 cm) Vigreaux column to remove the acetic acid/acetic anhydride (96 g.) over a boiling range of 44°–49° C. at 44 mm mercury pressure. The distillation residue was extracted 5 times with 75 ml portions of benzene and the benzene insoluble catalyst residue saved for use in the next Run (Run 2). The benzene extracts were combined and distilled at atmospheric pressure to remove 256 g. of benzene and at 8 mm mercury pressure to yield 21.6 g. of an oil boiling over a range of 78°–128° C. This oil was analyzed by gas-liquid phase chromatography (GLC).

In Run 2, the catalyst recovered from Run 1 was charged to the reactor with 2.3 g. (10.7 mmoles) 1,4-dibromo-2-butene and the amounts of acetic acid, acetic anhydride, and 1,3-butadiene shown in Table I. The reaction was conducted in essentially the same manner as described for Run 1.

At the conclusion of the reaction, the reactor was vented and the reaction mixture was distilled at 45 mm mercury pressure to remove 71 g. of acetic acid/acetic anhydride over a boiling range of 44°–49° C. The residue was extracted 5 times with 75 ml. portions of benzene and the catalyst residue was saved for use in the next Run (Run 3). The combined benzene extracts were distilled at atmospheric pressure to remove the benzene and at 8 mm mercury pressure to yield 22.4 g. of an oil boiling over a range of 74° to 128° C. The oil was analyzed by GLC.

In Run 3, the catalyst recovered from Run 2 was charged to the reactor with 1,4-dibromo-2-butene (4.6 g., 21.5 mmoles) and the amounts of acetic anhydride and 1,3-butadiene shown in Table I. The reaction was conducted in essentially the same manner as described in Run 1. At the conclusion of the reaction, the reactor was vented, and the reaction mixture was distilled at 50 mm mercury pressure to remove 98.2 g. of acetic acid/acetic anhydride over a boiling range of 43°–67° C. The residue was extracted 6 times with 75 ml portions of benzene and the combined benzene extracts were distilled at atmospheric pressure to remove 264 g. of benzene and at 8 mm mercury pressure to yield 19.5 g. of an oil boiling over a range of 67°–130° C.

Oil was analyzed by GLC. The results obtained from each Run are shown in Table I:

TABLE I

| Run No. | Acetic Acid, ml | Acetic Anhydride, ml | 1,3-Butadiene, mmole |
|---|---|---|---|
| 1 | 50 | 25 | 233.2 |

TABLE I-continued

| | | | |
|---|---|---|---|
| 2 | 65 | 25 | 200 |
| 3 | 0 | 75 | 233.3 |

| Run No. | Diacetoxybutene % Yield[a] | Isomer Distribution | | |
|---|---|---|---|---|
| | | 1,2 | cis-1,4 | trans-1,4 |
| 1 | 55.6 | 35 | 8 | 57 |
| 2 | 65.1 | 31 | 69[b] | |
| 3 | 46.1 | 34 | 66[b] | |

[a]Yield of combined diacetoxybutene isomers based on 1,3-butadiene charged.
[b]Values for cis- and trans- isomer content not individually determined in Runs 2 and 3.

The results shown in Table I demonstrate that catalyst recovered by the process of my invention can be recycled to another oxidation reaction with good results. Run 3 showed good yield even though this was the third run with the catalyst components (A) and (B), which had been augmented only by (C). Also, Run 3 employed the anhydride alone which generally results in slightly reduced yield as compared to a mixed carboxylic acid media.

EXAMPLE II

Runs 4 and 5 were carried out in a manner similar to Run 1 for an analysis of the benzene extracts to determine the amounts of catalyst components removed by the benzene extractions. In each Run, a 250 ml Fischer-Porter aerosol compatibility bottle equipped with a magnetic stirrer was charged with cupric acetate monohydrate (9.6 g., 48 mmoles), lithium bromide (6.5 g., 75 mmoles), 1,4-dibromobutene (4.6 g., 21.5 mmole), acetic acid (50 ml), and acetic anhydride (25 ml), followed by the addition of 1,3-butadiene (11.8 g., 218.5 mmoles in Run 4, or 12.5 g., 231.5 mmoles in Run 5) to the reactor in the vapor phase. The reactions were conducted in essentially the same manner as described in Run 1.

At the conclusion of each reaction, the reactor was vented and the reaction mixture was first distilled to remove acetic acid and acetic anhydride and then was extracted 4 times with 75 ml portions of benzene. The combined benzene extracts were analyzed and found to contain 21.2 and 18.7 mmoles bromide, 0.96 and 1.2 mmoles lithium, and 0.055 and 0.05 mmoles copper, each respectively Runs 4 and 5. These results show that only about 1.5% of the lithium and about 0.1% of the copper charged to the reactor were extracted and thus lost in the benzene extraction step.

EXAMPLE III

Run 6 was conducted according to my invention utilizing n-butyl chloride as the extraction solvent. In Run 6, a 250 ml Fischer-Porter aerosol compatibility bottle equipped with a magnetic stirrer was charged with cupric acetate monohydrate (9.6 g., 48 mmoles), lithium bromide (6.5 g., 75 mmoles), 1,4-dibromo-2-butene (4.6 g, 21.5 mmoles), acetic acid (50 ml), and acetic anhydride (25 g), followed by the addition of 1,3-butadiene (12.2 g., 225.9 mmoles) to the reactor in the vapor phase. The Run was conducted in a manner similar to that described in Run 1 of Example I.

At the conclusion of the reaction, the reactor was vented, and the reaction mixture was transferred to a distilling flask and distilled at 50 mm mercury pressure to remove 96 g. of acetic acid/acetic anhydride. The distillation residue was extracted 4 times with 75 ml portions of n-butyl chloride. The n-butyl chloride extracts were combined to yield 271.3 g. of a liquid extract.

Analysis of a portion of this liquid extract showed that it contained 31.5 mmoles bromide and 0.076 mmole copper (0.16% of the amount of copper charged to the reaction mixture) corrected for the total amount of extract. The level of lithium ion was below the detection limit of 2 ppm.

A 220.5 g. portion of the n-butyl chloride extract was distilled at atmospheric pressure to remove 198 g. solvent over a boiling range of 76°–80° C. and at 8 mm mercury pressure to remove 16.7 g. of an oil boiling over a range of 98°–134° C. A GLC analysis of the oil indicated that a 52.8% yield of diacetoxybutenes, corrected for the total amount of extract, based on the amount of 1,3-butadiene charged, was obtained.

The results of this run show that the process of my invention using an extraction solvent successfully separates the oxidation products from the catalyst with minimal removal (loss) of catalyst.

EXAMPLE IV

A series of control Runs was conducted to demonstrate the critical nature of the extraction solvent in the catalyst separation process of my invention. Each of these runs utilized a 250 ml Fischer-Porter aerosol compatibility bottle equipped with a magnetic stirrer as the reactor means, and used 50 ml acetic acid and 25 ml acetic anhydride. The indicated quantities of chemicals used and the procedure for the oxidation reaction were essentially the same as described in Run 1 of Example I.

In Run 7, the reaction mixture was distilled at 25 mm to remove 65.9 g. of a mixture of acetic acid and acetic anhydride and then was extracted 6 times with 75 ml portions of pentane. The combined pentane extracts were transferred to a distilling flask and the pentane was distilled at atmospheric pressure to leave 17.4 g. of an oil. The pentane insoluble catalyst residue from the pentane extraction was extracted 6 times with 75 ml portions of cyclohexane and the cyclohexane extracts were combined and distilled to leave 2.3 g. of an oil. The catalyst residue from the cyclohexane extractions was used in Run 8 and the two oils from the pentane and cyclohexane extractions were analyzed by GLC.

In Run 8, the catalyst residue from the pentane and cyclohexane extractions in Run 7 was used. The reaction mixture was transferred to a distilling flask and distilled to yield two fractions. Fraction 1 (acetic acid/acetic anhydride) was collected over a boiling range of 48°–65° C. at 50 mm mercury pressure and weighed 92.5 g. while fraction 2 was collected over a boiling range of 75°–128° C. at 8 mm mercury pressure and weighed 21.9 g. Fraction 2 was analyzed by GLC.

In Run 9, the reaction mixture was transferred to a distilling flask and 94 g. of acetic acid/acetic anhydride was distilled at 50 mm mercury pressure. The residue was extracted 4 times with 75 ml portions of cyclohexane. Analysis of the combined cyclohexane extracts showed low levels of copper (<3 ppm) and lithium (<10 ppm) ions. A 175.2 g. portion of the combined cyclohexane extracts was distilled through an 18" (46 cm) Vigreaux column at atmospheric pressure to yield 178 g. of cyclohexane boiling at 77°–78° C. and at 8 mm mercury pressure to yield 5.4 g. of an oil boiling over a range of 80°–126° C. The oil was analyzed by GLC.

In Run 10, the reaction mixture was poured into a mixture of water (400 ml) and ether (400 ml). An insoluble material formed which was filtered and air dried to yield 6.4 g. (solid no. 1). The layers were separated and the aqueous layer was evaporated to dryness to leave 11.1 g. of a dark solid (solid no. 2). Analyses of the two solids isolated during the workup showed that considerable amounts of lithium, copper, and bromine were present as shown in Table II:

TABLE II

|  | Lithium | | Copper | | Bromine | |
|---|---|---|---|---|---|---|
|  | % | mmole | % | mmole | % | mmole |
| Solid No.1 (Solid insoluble in both layers) | 0.03 | 3 | 34 | 34 | 35 | 28 |
| Solid No. 2 (Solid from aqueous layer) | 4.23 | 70 | 6.1 | 10.7 | 24 | 33.3 |

The ether layer was distilled at atmospheric pressure through a ¾" (19 mm)×15" (380 mm) column packed with 6 mm Raschig rings to remove the ether. The distillation residue was distilled at 50 mm mercury pressure to remove 76.4 g. (fraction 1) over a boiling range of 46°–71° C. and at 8 mm mercury pressure to remove 22.8 g. (fraction 2) over a boiling range of 78°–128° C. Fraction 2 was analyzed by GLC.

The amounts of catalyst components and 1,3-butadiene used in each Run, and the results obtained by GLC analyses in each of the Runs, are shown below in Table III:

TABLE III

| Run No. | Cu(OAc)$_2$/ H$_2$O mmole | LiBr, mmole | 1,4-Dibromo-2-butene mmole | 1,3-Butadiene, mmole |
|---|---|---|---|---|
| 7 | 48 | 75 | 10.7 | 222.2 |
| 8 | (a) | — | 10.7 | 218.7 |
| 9 | 48 | 75 | 21.5 | 225.9 |
| 10 | 48 | 75 | 10.7 | 229.6 |

| Run No. | Extractant | Diacetoxybutenes % Yield[b] | Isomer Distribution | |
|---|---|---|---|---|
|  |  |  | 1,2- | cis- & trans-1,4- |
| 7 | Pentane | 39[c] | 52 | 48 |
|  | Cyclohexane | 45[d] | 50 | 50 |
| 8 | — | 58 | 38 | 62 |
| 9 | Cyclohexane | 14 | 44 | 56 |
| 10 | Water/ether | 56[e] | 34 | 66 |

[a]The catalyst recovered from the previous reaction was used in this run.
[b]Yield of combined diacetoxybutene isomers based on 1,3-butadiene charged.
[c]Yield isolated by pentane extraction.
[d]Total yield isolated by both pentane and cyclohexane extractions.
[e]The product also included 7.5% of 4-vinyl-4-butyrolactone.

The results of these Runs show that several other extraction solvents are less useful than the solvents described according to my invention. The low solubility exhibited by the oxidation products in pentane (Run 7) or cyclohexane (Run 9) would require excessive quantities of solvent for satisfactory removal of oxidation products. An attempted extraction using water and ether (Run 10) was found to be impractical because of precipitation of substantial quantities of copper containing salts which would require a slow filtration step before phase separation.

EXAMPLE V

A series of Runs was conducted with benzene as the extraction solvent to demonstrate the process of my invention with a catalyst system of antimony oxide, lithium bromide, and 1,4-dibromo-2-butene. In each Run a 250 ml Fischer-Porter aerosol compatibility bottle equipped with a magnetic stirrer was used as the reactor.

In Run 11, antimony oxide (2.9 g., 10 mmoles), lithium bromide (6.5 g., 75 mmoles), 1,4-dibromo-2-butene (4.6 g., 21.5 mmoles), acetic acid (50 ml), and acetic anhydride (25 ml), were charged to the reactor, followed by the addition of 1,3-butadiene (11.4 g., 211.1 mmoles) to the reactor in the vapor phase. The oxidation reaction was conducted in a manner similar to the procedure described in Run 1 of Example I. At the conclusion of the reaction, the reactor was vented, and the reaction mixture was transferred to a distillation flask and distilled at 50 mm to remove 78 g. of acetic acid/acetic anhydride over a boiling range of 45°–65° C. The distillation residue was extracted 6 times with 75 ml portions of benzene and the extraction residue was saved for use in Run 12. The benzene extracts were combined, distilled at atmospheric pressure to remove benzene, and then distilled at 8 mm mercury pressure to yield 22 g. of distillate. A GLC analysis of the distillate showed that a 60.2% yield of diacetoxybutenes based on the amount of 1,3-butadiene charged was obtained. The diacetoxybutene isomer distribution was 22% 1,2-diacetoxy-3-butene and 78% cis- and trans-1,4-diacetoxy-2-butene.

In Run 12, the catalyst residue from Run 11, together with 1,4-dibromo-2-butene (4.6 g., 21.5 mmoles), acetic acid (50 ml), and acetic anhydride (25 ml), were charged to the reactor, followed by the addition of 1,3-butadiene (12.4 g., 229.6 mmoles) in the vapor phase. The oxidation reaction was conducted in a manner similar to the procedure used in Run 11. At the conclusion of the reaction, the reactor was vented, and the reaction mixture was transferred to a distilling flask and distilled through an 18" (46 cm) Vigreaux column. The first fraction (85.5 g) acetic acid/acetic anhydride was collected over a boiling range of 45°–60° C. at 50 mm mercury pressure, and the second fraction (34 g.) was collected over a boiling range of 70°–129° C. at 8 mm mercury pressure. A GLC analysis of the second fraction showed a yield of 86.1% of diacetoxybutene isomers (24% 1,2-diacetoxy-3-butene, 76% cis- and trans-1,4-diacetoxy-2-butenes) based on the amount of 1,3-butadiene charged.

Runs 13 and 14 were conducted to determine the amounts of antimony and lithium which dissolved in the benzene extracts during the oxidation product extraction. The quantities used were the same as in Run 11 except for the use of in Run 13 12.6 g., 233 mmoles and Run 14 12.4 g. 229 mmoles of 1,3-butadiene. The reaction mixtures were distilled at 50 mm (Run 13), and 30 mm (Run 14), mercury pressure to remove the acetic acid/acetic anhydride, and were then extracted 4 times with 75 ml portions of benzene. Analyses of the combined benzene extracts in each run are shown below.

TABLE IV

|  | Antimony | | Lithium | | Bromine | |
|---|---|---|---|---|---|---|
|  | % | mmole | ppm | mmole | % | mmole |
| Run 13 | 0.008 | 8.18 | 47 | 1.8 | 1.07 | 36 |
| Run 14 | 0.015 | 0.32 | 28 | 1.1 | 1.17 | 38 |

The results of these Runs demonstrate that the process of my invention with benzene as the extraction solvent successfully separates the oxidation products from the catalyst with minimal loss of the antimony and lithium components of the catalyst. The recovered catalyst is suitable for recycling to the oxidation step with no apparent loss of activity.

Product Utility

The diacycloxy olefins which are recovered from the product mixture include, in many instances, an amount of 1,2-isomer, which can be separated by such as distillation and recycled to the reaction zone for conversion to the more desired 1,4-diacyloxy olefin.

The 1,4-diacyloxy olefins are useful as intermediates for the preparation of the corresponding saturated diols, such as, for example, 1,4-butanediol, a valuable intermediate used in the preparation of polybutylene terephthalate, an engineering-type plastic. British Pat. No. 1,170,222 describes the preparation of tetrahydrofuran, starting with conjugated dienes and proceeding through the 1,4-diacyloxybutenes. Tetrahydrofuran itself, of course, is produced when starting with 1,3-butadiene. The saturated diols, such as 1,4-butanediol and tetrahydrofurans, have known utility in the chemical arts.

This disclosure, including data, has illustrated the value and effectiveness of my invention. The examples, the knowledge and background of the field of the invention and of general prinicples of chemistry and other applicable sciences, have formed the bases to which the broad descriptions of the invention, including the ranges of conditions and generic groups of operant components have been developed, and formed the bases for my claims here appended.

I claim:

1. A process for the production of diacycloxy olefins which comprises:
   (a) oxidizing at least one acyclic conjugated diolefin with molecular oxygen under oxidation reaction conditions in carboxylic acid reactant media employing a catalyst system comprising (A) at least one copper or antimony compound, (B) at least one alkali metal compound, (C) a halide ion-source wherein said halide is bromide or chloride, thereby preparing a product reaction mixture comprising at least one diacycloxy olefin, catalyst residues, unreacted diolefin, residual oxygen, and residual carboxylic acid media,
   wherein said acyclic conjugated diolefin is selected from unsubstituted and substituted diolefins of 4 to 16 carbon atoms wherein the substituents are selected from the group consisting of halogen, cyano, —COOR', and hydrocarbyl radicals, wherein R' is hydrogen or an alkyl or aryl radical; and
   said carboxylic acid media is selected from the group consisting of mono- and dicarboxylic aliphatic, cycloaliphatic, and aromatic acids, corresponding anhydrides, and mixtures, having 2 to 18 carbon atoms per molecule;
   wherein said (A) where copper is selected from the group consisting of copper chlorides, bromides, oxides, carbonates, carboxylates, nitrates, orthophosphates, sulfates, and mixtures; and where antimony is selected from the group consisting of the chlorides, bromides, oxides, carboxylates, nitrates, sulfates, and mixtures;
   said (B) is selected from the group consisting of the halides, nitrates, carboxylates, oxides, hydroxides, carbonates, orthophosphates, and sulfates, of lithium, sodium, potassium, rubidium, and cesium, and mixtures;
   and said (C) halide-source is a said (A) or (B) where said (A) or (B) is the halide, alkaline earth metal halides, or diolefin;
   (b) venting said product reaction mixture of any light unreacted components including residual oxygen, leaving a stripped reaction mixture,
   (c) fractionating said stripped reaction mixture, thereby distilling off streams comprising said residual carboxylic acid media, and unreacted diolefin not vented, leaving a remaining reaction mixture comprising diacyloxy olefin product and catalyst residues,
   (d) extracting said remaining reaction mixture with an effective amount of a solvent in which said diacyloxy olefin product exhibits a high degree of solubility, and said catalyst residues exhibit a low solubility, thereby forming an extract containing said diacyloxy olefin product, and a extraction residue containing said catalyst residues, wherein said solvent is normally liquid and consists of aliphatic halohydrocarbons or unsubstituted or alkyl-substituted aromatic solvents, or mixtures thereof,
   (e) recycling said separated carboxylic acid media from said step (c) to said step (a),
   (f) recycling extraction residue containing said catalyst residues to said step (a),
   (g) separating said diacyloxy olefin product from said extract, leaving a recovered solvent, and
   (h) recycling said recovered solvent to said step (d).

2. The process according to claim 1 wherein said acyclic conjugated diolefin is selected from the group consisting of 1,3-butadiene, 2-methyl-1,3-butadiene, 2-chloro-1,3-butadiene, 2-ethyl-1,3-butadiene, 2-chloro-3-methyl-1,3-butadiene, 1,4-diphenyl-1,3-butadiene, 1,3-hexadiene, 1,3-pentadiene, 1,3-octadiene, 2-cyano-1,3-butadiene, 2-cyclohexyl-1,3-butadiene, 2-methylene-3-butenoic acid, and 2,4-pentadienenitrile.

3. The process according to claim 2 wherein said copper compound is selected from the group consisting of copper(II) acetate, copper(I) bromide, copper(II) bromide, copper(II) benzoate, copper(II) butanoate, copper(I) chloride, copper(II) chloride, copper(II) dodecanoate, copper(II) octadecanoate, copper(I) oxide, copper(II) salicylate, copper(I) carbonate, copper(I) sulfate, copper(II) sulfate, copper(II) nitrate, and copper(II) orthophosphate.

4. The process according to claim 2 wherein said (A) is antimony tribromide, antimony trichloride, antimony pentachloride, antimony pentoxide, antimony trioxide, antimony (III) sulfate, or antimony trinitrate, or mixture.

5. The process according to claim 1 wherein said (C) halide ion source is at least in part provided by at least one of an alkali metal halide, alkaline earth metal halide, or dihaloolefin.

6. The process according to claim 1 wherein said acid reactant media monocarboxylic acid is represented by R"—COOH,
   and said dicarboxylic acid is represented by R'"(COOH)$_2$,
   wherein said R" is selected from the group consisting of alkyl, cycloalkyl, aryl, and combination radicals, and halogen, cyano, and —COOR' substituted derivatives thereof wherein up to 4 of said halogen, cyano, or —COOR' substituents can be present in said R" radical,
   said R'" is selected from the group consisting of a valence bond, and alkylene, cycloalkylene, arylene, or combination radicals, and halogen, cyano, and —COOR' substituted derivatives of said radicals wherein up to 4 of said halogen, cyano, or —COOR' substituents can be present in said R''' radical, and wherein R' is selected from the group consisting of hydrogen, an alkyl radical of up to 10 carbon atoms, and an aryl radical of up to 10 carbon atoms.

7. The process according to claim 6 wherein said carboxylic acid reactant media is a monocarboxylic acid, optionally with an anhydride, selected from the group consisting of acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, 2-bromobutanoic acid, ethyl hydrogen adipate, 4-chlorobenzoic acid, 2-cyclohexylbenzoic acid, 2,3,4,5-tetrachlorobenzoic acid, ethyl hydrogen-o-phthalate, 4,6,8,10-tetracyanoundecanoic acid, 4,6,8,10-tetramethoxycarbonylundecanoic acid, 4-decyloxycarbonylcyclohexanecarboxylic acid, the corresponding anhydrides, and mixtures.

8. The process according to claim 6 wherein said carboxylic acid reactant media is a dicarboxylic acid, optionally with an anhydride, selected from the group consisting of oxalic acid, succinic acid, terephthalic acid, adipic acid, tetrabromo-1,4-benzenedicarboxylic acid, tetracyano-1,4-benzenedicarboxylic acid, tetramethoxycarbonyl-1,4-benzenedicarboxylic acid, 2-decyloxycarbonylhexanedioic acid, the corresponding anhydrides, and mixtures.

9. The process of claim 1 employing said (A) copper or antimony compound in the range of about 0.01 to 1 mole per mole of acyclic conjugated diene;

a molar ratio of (B):(A) alkali metal compound:copper or antimony in the range of about 0.1:1 to 100:1;

a molar ratio of (C):(A) halide:copper or antimony in the range of about 0.1:1 to 100:1;

and employing said carboxylic acid reactant media in a molar range from about equimolar up to about 500:1 based on acyclic conjugated diene.

10. The process of claim 9 employing said (A) copper or antimony compound in the range of about 0.02 to 0.5 mole per mole of acyclic conjugated diene;

a molar ratio of (B):(C) alkali metal compound:copper or antimony compound in the range of about 1:1 to 10:1;

a molar ratio of (C):(A) halide component:copper or amtimony component in the range of about 1:1 to 15:1;

and employing said carboxylic acid reactant media in a molar range of about 2:1 to 10:1.

11. The process according to claim 1 employing said anhydride as a component of said carboxylic acid reactant media in the range of about 0.01 to 5 moles of anhydride per mole of organic acid.

12. The process according to claim 1 wherein said extracting solvent is benzene, toluene, o-xylene, m-xylene, p-xylene, chloroform, carbon tetrachloride, methylene chloride, n-propyl chloride, n-butyl chloride, n-butyl bromide, 1-chlorohexane, 2-chlorohexane, 1,2-dichloroethane, 1,1,2,2-tetrachloroethane, 1,1,2,2-tetrachlorohexane, cyclohexyl bromide, cyclohexyl chloride, 1,2-dichlorocyclohexane (cis- or trans-), 1-chlorooctane, 1-bromooctane, 1-chlorododecane, or mixture.

13. The process according to claim 12 employing about 0.5 to 50 volumes of said extractive solvent per volume of oxidation product.

14. The process according to claim 1 wherein said oxidation step (a) is conducted at a reaction temperature in the range of about +30° C. to 200° C., substantially in the liquid phase, for about 1 to 18 hours.

15. The process according to claim 14 wherein said acyclic conjugated diene is 1,3-butadiene, said catalyst comprises cupric acetate, lithium bromide, and 1,4-dibromo-2-butene, employing at least one of acetic acid and acetic anhydride as said carboxylic acid reactant media, and benzene as said extraction solvent.

16. The process according to claim 14 wherein said acyclic conjugated diene is 1,3-butadiene, said catalyst comprises cupric acetate, lithium bromide, and 1,4-dibromo-2-butene, employing at least one of acetic acid and acetic anhydride as said carboxylic acid reactant media, and n-butylchloride as said extraction solvent.

17. The process according to claim 1 further recycling from said step (b) unreacted acyclic conjugated diene to said step (a).

18. The process according to claim 1 further treating said catalyst residues from said step (d) with a drying gas to strip traces of residual extractive solvent prior to returning the resulting treated recovered catalyst residues to oxidation step (a).

19. The process according to claim 1 further comprising (i) fractionally distilling said diacyloxy olefin product to recover a purified diacyloxy olefin.

* * * * *

UNITED STATES PATENT AND TRADEMARK OFFICE
CERTIFICATE OF CORRECTION

PATENT NO. : 4,237,312

DATED : Dec. 2, 1980

INVENTOR(S) : Paul R. Stapp

It is certified that error appears in the above-identified patent and that said Letters Patent are hereby corrected as shown below:

Claim 1, col. 14, in the "(d)" section, line 18, after "and" and before "extraction" should be --- an --- instead of "a".
Claim 5, col. 14, line 53, there should be a hyphen before "ion" making it "halide-ion".
Claim 10, col. 16, line 2, "antimony" is misspelled, and "component" should be removed and --- compound --- inserted.
Claim 18, col. 16, line 46, "oxidation" should be deleted.

Signed and Sealed this

Twenty-eighth Day of April 1981

[SEAL]

Attest:

RENE D. TEGTMEYER

Attesting Officer     Acting Commissioner of Patents and Trademarks